United States Patent [19]

Alink

[11] Patent Number: 5,034,161

[45] Date of Patent: Jul. 23, 1991

[54] SYNTHESIS OF ARYL-SUBSTITUTED ALIPHATIC ACIDS

[75] Inventor: Bernardus A. O. Alink, St. Louis, Mo.

[73] Assignee: Petrolite Corporation, St. Louis, Mo.

[21] Appl. No.: 226,242

[22] Filed: Jul. 18, 1988

[51] Int. Cl.$^5$ ............................................. C11C 11/00
[52] U.S. Cl. ................................. 260/413; 585/455; 585/456
[58] Field of Search ........................................ 260/413

[56] References Cited

U.S. PATENT DOCUMENTS

| | | | |
|---|---|---|---|
| 3,282,973 | 11/1966 | Devine | 260/413 |
| 3,476,785 | 11/1969 | Huelsmann et al. | |
| 3,845,089 | 10/1974 | Henrick | 260/413 |
| 4,038,213 | 7/1977 | McClure et al. | 252/430 |
| 4,614,816 | 9/1986 | Drury et al. | 260/413 |

OTHER PUBLICATIONS

"Heterogeneous Catalysis by Solid Superacids, Alkylation of Benzene and Transalkylation of Alkylbenzenes over Graphite-Intercalated Lewis Acid Halide and Perfluorinated Resin-Sulfonic Acid (NAfion-H) Catalysts", George A. Olah, Joseph Kapsi, and Josef Bukala, J. Org. Chem., vol. 42, No. 26, 1977 (pp. 4187–4191).
"Heterogeneous Catalysis by Solid Superacids, Methylation of Phenols with Methyl Alcohol and the Rearrangement of Anisole and Methylanisoles over a Perfluorinated Resinsulfonic Acid (Nafion-H) Catalyst", Joseph Kaspi and George A. Olah, J. Org. Chem., vol. 43, No. 16, 1978 (pp. 3142–3150).
"Firedel-Crafts Alkylation of Benzene, Alkylbenzenes and Halobenzenes with Alkyl Halides Over a Perfluorinated Resinsulfonic Acid (nafion-H) Catalyst", George A. Olah and David Meidar, Nouveau Journal de Chime, vol. 3, No. 4, 1979 (pp. 269–273).
"Methanesulfonic Acid Catalyzed Addition of Aromatic Compounds to Oleic Acid", Y. Nakano and T. A. Foglia, JAOCS, vol. 61, No. 3 (Mar. 1984).
Nafion Superacid Catalysts, Type NR50, Safety in Handling and Use, Dupont Brochure, Jul. 1986.
Methanesulfonic Acid Catalyzed Addition of Aromatic Compounds to Oleic Acid by Y. Nakano and T. A. Foglia, JAOCS, vol. 61, No. 3, 3/84.

Primary Examiner—Patrick P. Garvin
Assistant Examiner—E. D. Irzinski
Attorney, Agent, or Firm—Robert E. Wexler; Jeffrey S. Boone; Stanley M. Tarter

[57] ABSTRACT

A method for preparation of aryl-substituted aliphatic hydrocarbons is disclosed. The method comprises reacting in the presence of a solid superacid resin catalyst an unsaturated aliphatic hydrocarbon in liquid form with an aromatic hydrocarbon that is susceptible to Friedel-Crafts reaction. The reaction between the liquid unsaturated aliphatic hydrocarbon and the aromatic hydrocarbon produces a reaction product comprising an aryl-substituted aliphatic hydrocarbon.

11 Claims, No Drawings

SYNTHESIS OF ARYL-SUBSTITUTED ALIPHATIC ACIDS

BACKGROUND OF THE INVENTION

1. Field of the Invention

The present invention relates to aryl-substituted aliphatic hydrocarbons, and more particularly to methods for preparation of aryl-substituted aliphatic acids from unsaturated aliphatic hydrocarbons and aromatic hydrocarbons.

2. Description of the Prior Art

Conventional methods for preparation of aryl-substituted aliphatic acids suffer from several drawbacks. For example, standard methods not only have involved production of complex reaction mixtures and required expensive and cumbersome separation techniques, but also result in low yields. Such aryl-substituted aliphatic acids are particularly useful as corrosion inhibitors or as substrates for corrosion inhibitors. Saturated fatty acids have been considered for such uses; but they are ordinarily solids which are insoluble in the oil products, such as motor oil, for which the inhibitors are desired. Thus, branched acids, such as isostearic acid, sometimes have been used. However, due to the drawbacks of the conventional methods for preparation of branched acids, such acids are expensive.

Typically, a Friedel-Crafts reaction has been the vehicle for preparation of aryl-substituted saturated acids. According to this reaction, an aromatic hydrocarbon, such as benzene or toluene, is reacted in the presence of an acidic reagent with an unsaturated aliphatic acid, for example, oleic acid. The acidic reagent employed in this process is a strong Lewis acid, commonly aluminum chloride, boron trifluoride or hydrofluoric acid. For example, in Nakano, Y. and Foglia, T. A., "Methanesulfonic Acid Catalyzed Addition of Aromatic Compounds to Oleic Acid," JAOCS, Vol. 61, No. 3 (March 1984), the use of aluminum chloride to catalyze a reaction between benzene and oleic acid is noted.

Such methods involve several disadvantages. For example, since the Lewis acids employed in the Friedel-Crafts reaction are extremely strong acids and are extremely reactive, and because hydrogen halide gas is generated, special handling and extra safety precautions are required. In addition, the reaction is exothermic and must be moderated by cooling. Further, the Lewis acid is consumed in the reaction, making recycling of the acid impossible and adding significantly to the cost of the reaction. Moreover, such methods produce inferior yields when the aliphatic acid is internally unsaturated.

In addition, the reaction also is associated with several undesirable side reactions, resulting in limited yields and separation problems. Morever, for example, since one such side reaction is polyalkylation, a substantial excess of the aromatic hydrocarbon is commonly employed in an effort to limit polyalkylation of the aromatic ring. However, such efforts to limit polyalkylation have proven unsatisfactory since use of a substantial excess of the aromatic hydrocarbon tends to increase costs of the process and, in any event, polyalkylation is not entirely eliminated by such measures.

According to other side reactions, where an acid such as oleic acid is employed as an aliphatic hydrocarbon substrate in the reaction, the intermediate carbonium ion reacts with the carboxyl group of the acid to form lactones. If an unsaturated acid is employed as the aliphatic hydrocarbon substrate, the intermediate carbonium ion may also react with two acid molecules to yield an ester of the acid. As a result of the involvement of such side reactions, the yield of the desired product is diminished and the reaction product comprises a mixture of compounds, requiring extensive purification techniques to isolate the desired mono-substituted alkyl aromatic.

Moreover, many procedures required by the conventional reaction prove very troublesome in practice. The reaction products are darkly colored, making separation and isolation difficult; and steam distillation is often necessary to isolate the desired products. In addition, the products obtained are complex mixtures; and their complex structure adds to the difficulty in purification. Not only that, but also the excess highly reactive Lewis acid which is employed in the reaction as a catalyst must be carefully quenched.

Further, the physical properties of the reaction product are often not suitable for the desired applications. For example, the typical reaction yields a high melting solid, when commercial application, for example, as a corrosion inhibitor or substrate therefor, requires a low melting solid or a liquid. Thus, an improved method for preparation of suitable branched fatty acids is needed.

The Nakano and Foglia article noted above describes a method for adding aromatic compounds to the double bond of oleic acid by a methanesulfonic acid catalyzed reaction. However, the reaction described therein requires copious amounts of methanesulfonic acid (6:1 molar ratio based on oleic acid content) and produces yields significantly under 80%, resulting in a difficult separation process involving a two-step extraction/water washing technique and a relatively expensive process. Moreover, the significant interplay of undesirable side reactions in the Nakano and Foglia method results in a product containing large amounts of impurities, especially lactones and esters of oleic acid. Accordingly, the industry is still searching for satisfactory methods for preparation of aryl-substituted aliphatic hydrocarbons.

SUMMARY OF THE INVENTION

Briefly, therefore, the present invention is directed to a novel method for preparation of aryl-substituted aliphatic hydrocarbons. The method comprises reacting in the presence of a solid superacid resin catalyst an unsaturated aliphatic hydrocarbon in liquid form with an aromatic hydrocarbon that is susceptible to Friedel-Crafts reaction. The reaction between the liquid unsaturated aliphatic hydrocarbon and the aromatic hydrocarbon produces a reaction product comprising an aryl-substituted aliphatic hydrocarbon.

Among the several advantages found to be achieved by the present invention, therefore, may be noted the provision of a method for the alkylation of aromatic hydrocarbons with unsaturated acids to produce an aryl-substituted aliphatic hydrocarbon in high yield with little or no side products; the provision of such method which employs a catalyst that is not extremely reactive, is not difficult to handle, and that can be recycled; the provision of such method which does not entail procedures that tend to be very troublesome in practice; and the provision of such method which is particularly suitable for alkylation of aromatic hydrocarbons with unsaturated acids which are internally unsaturated.

DESCRIPTION OF THE PREFERRED EMBODIMENTS

In accordance with the present invention, it has been discovered that reacting, in the presence of a solid superacid resin catalyst, a liquid unsaturated aliphatic hydrocarbon with an aromatic hydrocarbon produces a nearly quantitative yield of aryl-substituted aliphatic hydrocarbon. Surprisingly, it has been found that this very simple, straightforward reaction not only produces yields of the desired product in excess of 80%, and often approaching 100%, and little if any side product, but also requires very simple, relatively trouble-free procedures and only a single, simple separation step, preferably by decanting or screening, to produce a high quality commercial product. Such product has been found to be particularly suitable as a corrosion inhibitor, or substrate therefor. The corrosion inhibitors derived from such products are low-melting solids or are liquids, and are well adapted for use in oil systems.

Moreover, the catalyst employed in the method of this invention is a true catalyst which may be reused repeatedly, and does not require the handling precautions required by the acids used in a standard Friedel-Crafts reaction. The effectiveness and advantages of solid superacid resin catalysts are particularly surprising in view of the fact that similar resin-type catalysts have been found to be unsatisfactory.

It is believed that virtually any unsaturated aliphatic hydrocarbon may in liquid form be employed in the method of this invention. Therefore, aliphatic hydrocarbons which may be employed in the method of this invention are liquids which correspond to the formula

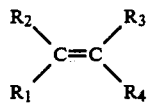

wherein $R_1$, $R_2$, $R_3$, and $R_4$ are independently selected from among nearly any radical, including hydrogen, halides, amino groups, alkyl groups and aryl groups, and substituted alkyl and aryl groups. The liquid form of the hydrocarbon may be by virtue of the natural liquid state of the hydrocarbon or, if the hydrocarbon is naturally solid, as a result of melting the hydrocarbon or dissolving the hydrocarbon in an aromatic solvent such as toluene. If the hydrocarbon is a gas, the liquid form may be achieved by compressing the gas to a liquid state or by dissolving the hydrocarbon in toluene or other aromatic.

The method of the present invention involves a reaction at a localized reaction center, i.e., the double bond between successive carbon atoms, in the aliphatic hydrocarbons. Accordingly, so long as the hydrocarbon is a liquid, the substituents that are not involved in the reaction, that is, $R_1$, $R_2$, $R_3$ and $R_4$, may vary widely without departing from the scope of the invention. The identity of the particular substituents are, of course, determined by the formula of the desired reaction product. However, it has been found the process of this invention is particularly suitable for use with aliphatic hydrocarbons having internal unsaturation. Prior art processes have been particularly inadequate for application to such hydrocarbons. Accordingly, the present process is especially desirable for any mono-, di- or polyolefin having internal unsaturation, i.e., unsaturation at any point other than the terminal (alpha or omega) positions. The olefin may or may not also have terminal unsaturation, as desired. Thus, it is most desirable in the process of this invention that at least one substituent attached the carbon at each side of the double bond (at least one of $R_1$ and $R_2$ and at least one of $R_3$ and $R_4$) be a carbon-containing radical, such as an alkyl, aryl, substituted alkyl or substituted aryl group.

However, as discussed below, liquid, oil-soluble, oxidation resistant corrosion inhibitors or substrates therefor are particularly desirable products of the present method, and certain branched saturated acids have been found to be particularly suitable as such. In order to produce such branched acids, at least two of the radicals $R_1$, $R_2$, $R_3$, and $R_4$ should be alkyl or aryl groups.

Thus, for example, any olefin, including but not limited to, mono-olefins such as isobutylene, 2-olefins, propylene, butene, pentene, hexene, octene, nonenes and dodecene and diolefins such as butadienes and isoprenes, may be employed. Unsaturated fatty acids have been found to be particularly desirable aliphatic hydrocarbons for this invention. Unsaturated fatty acids which may be utilized include, for example, oleic acid, linoleic acid or linolenic acid, or esters of such acids, e.g., methyl oleate, methyl linoleate or methyl linolenate. Unsaturated oils, such as, rape seed oil, palm oil, soybean oil, safflower oil, tung oil, peanut oil, whole oil, menhaden oil, corn oil, cottonseed oil and olive oil, likewise are suitable for use in the reaction.

The aromatic hydrocarbon may be any aromatic that is susceptible to the typical Friedel-Crafts reaction. Accordingly, aromatic hydrocarbons at least as reactive as halobenzene may be employed in the reaction of this invention. On the other hand, aromatic hydrocarbons having a deactivating group such as a nitro group are not susceptible to the reaction of this invention. Thus, for example, aromatic hydrocarbons such as nitrobenzene are not appropriate aromatics for this method.

While, subject to the above-noted conditions, any aromatic hydrocarbon, whether benzenoid, nonbenzenoid, heterocyclic or otherwise, are understood to be suitable for use in the method of the present invention, in view of the particular corrosion inhibitors or substrates therefor that are desired products of the method, benzenoid compositions are preferred. Examples of suitable aromatic hydrocarbons, therefore, include benzene, alkylbenzenes, toluene, ethylbenzene, naphthalene, anthracene, alkylnaphthalene, alkylanthracenes, and commercially available linear alkylbenzenes and branched-chain alkylbenzenes. Substituted aromatic hydrocarbons, e.g., phenol, halobenzenes and thiophenol, are also suitable in this reaction.

The superacid resin catalyst of this invention has very high acidity and high thermal and chemical stability, is hydrophilic, and rapidly absorbs water and polar aromatics. For ease of separation from the reaction product, the catalyst is a solid and is insoluble in the reaction mixture. Thus, for example, the catalyst may be in the form of beads, tubing or membranes. It is desirable that the catalyst be in a form which has a high surface to volume ratio so that it provides exposure to a relatively large surface area. Beads have been found particularly useful in this respect. However, beads of sufficient size to allow separation by screening are especially desirable.

A superacid catalyst which has been found useful is NAFION ® catalyst, sold by E. I. du Pont. NAFION catalyst has a fluorocarbon backbone chain with perfluoro side chains containing sulfonic acid groups, with a chemical structure:

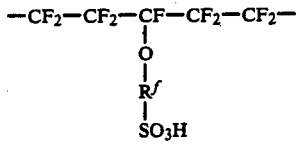

wherein $R^f$ is a perfluoro carbon radical. The sulfonic acid groups are essentially immobile and immersed in a fluorocarbon matrix.

The method or preparation of the aryl-substituted aliphatic acid may utilize almost any reaction process, whether a batch or flow process. The aromatic hydrocarbon and the aliphatic hydrocarbon are mixed together in the presence of the catalyst. The aliphatic hydrocarbon may be pre-mixed with a portion of the aromatic. This is particularly desirable if the aliphatic hydrocarbon is a solid—an amount of the aromatic may be used as a solvent and the aliphatic therefore may be dissolved in the aromatic solvent. If desired, the aromatic hydrocarbon may be refluxed with the catalyst to remove water, if any, from the catalyst, and then the aliphatic hydrocarbon may be added.

Since the reaction produces a nearly quantitative yield, with an aryl group being added to each double bond of the aliphatic hydrocarbon, the aromatic hydrocarbon is mixed with the aliphatic hydrocarbon in a molar ratio corresponding to the number of double bond in the aliphatic hydrocarbon. Thus, if the aliphatic hydrocarbon to be employed has a single double bond per molecule, at least one mole of aromatic per mole aliphatic hydrocarbon is used, and if the aliphatic hydrocarbon has two double bonds per molecule, at least two moles of aromatic hydrocarbon per mole aliphatic hydrocarbon are used. If a mixture of aliphatic hydrocarbon is used, then the amount of aromatic is related to the effective number of double bonds.

An excess of aromatic hydrocarbon may be desirable to enhance a dual role of the aromatic hydrocarbon—as a solvent and as a reactant. However, the amount of excess aromatic hydrocarbon needed to enhance this dual role is significantly less than the copious amounts used in attempts to inhibit polyalkylation in prior art methods. The excess aromatic may ultimately be removed from the reaction product by distillation or evaporation.

The amount of catalyst employed depends on the desired reaction rate with the rate increasing with higher catalyst content, but generally is in the range of from about 0.5% by weight to about 5% by weight based on total reaction mixture.

The reaction mixture is heated for about six to about eight hours. If the catalyst is a NAFION catalyst, the reaction temperature should be less than about 200° C. to avoid degradation of the NAFION catalyst or like perfluorinated sulfonic acids. The reaction may be conducted by refluxing the aromatic hydrocarbon and the aliphatic hydrocarbon under azeotropic conditions for several hours. It has been found that where the aromatic is toluene, a temperature of about 115° C. is desirable, and if the aromatic is benzene, a temperature of about 80° C. is desirable. If pressures exceeding atmospheric are applied, higher temperatures may be used.

The reaction product may then be cooled and separated from the catalyst. If the catalyst is in the form of beads, separation may be performed merely by, for example, decanting or straining. Then, excess aromatic hydrocarbon, if any, may be removed by distillation or simply by evaporation, as with a rotary evaporator. Yields in excess of about 80%, often near 100%, based on the amount of aliphatic hydrogen added, have been observed.

The isolated reaction product thus-produced generally is a light-colored, branched saturated acid. It is in a low melting solid or a liquid form, usually an oil, and typically requires no further purification. Products made in this manner, such as toluyl-stearic acid prepared from toluene and oleic acid, may be useful, for example, as corrosion inhibitors or as raw materials for preparation of corrosion inhibitors. Such inhibitors have been found to have greater oxidation stability than other commonly employed inhibitors, which typically are not branched compositions. Moreover, since inhibitors derived from the compositions prepared by the method of this invention or liquids or low melting solids, they are easily blended with oils such as motor oil to inhibit corrosion in oil systems. By contrast, saturated fatty acids tend to be insoluble solids.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples. In the examples all percentages are given on a weight basis unless otherwise indicated.

EXAMPLE I

Toluene (100 g.) was refluxed with NAFION (NR-50, E. I. du Pont) (25.5 g.) under azeotropic conditions. Approximately one milliliter of water was collected. The reaction mixture was then cooled to room temperature, and oleic acid (Pamolyn 125) (25.2 g.) was added. The mixture was refluxed for 7.5 hours. The final solution was very clear, with no evidence of any dark products. After cooling to room temperature, the resulting solution was decanted from the catalyst. The catalyst was washed 10 times with toluene (30 ml. doses). The toluene was evaporated from the product under reduced pressure, yielding a clear oil (26.6 g.). This oil had an acid number of 135.8 milliequivalents per gram, and gas chromatographic analysis showed 83% tolyl-stearic acid and 6% oleic acid.

EXAMPLE II

Cumene (15.5 g.) was reacted with oleic acid (Pamolyn-100) (2 g.) and NAFION (NR-50, E. I. du Pont) (2 g.), according to the method of Example I. The mixture was refluxed for 20 hours, and cooling and separation were performed as in Example I. A clear oil representing a yield of cumylstearic acid in excess of 80% based on oleic acid reactant was obtained.

EXAMPLE III

Phenol (10.3 grams) was reacted with oleic acid (Pamolyn-100) (28.4 g.) and NAFION (NR-50, E. I. du Pont) (5.3 g.), using a xylene mixture (20 g.) as the refluxing solvent. Cooling and separation were carried out as in Example I. A clear oil was obtained. Gas chromatographic analysis showed the oil to comprise only one compound, phenoxy stearic acid, representing a yield of greater than 80% based on oleic acid reactant.

In view of the above, it will be seen that the several advantages of the invention are achieved and other advantageous results attained.

As various changes could be made in the above methods and compositions without departing from the scope of the invention, it is intended that all matter contained in the above description shall be interpreted as illustrative and not in a limiting sense.

What is claimed is:

1. A method of preparing an aryl-substituted saturated higher fatty acid compound comprising bringing into reactive contact an unsaturated higher fatty acid compound and an aromatic compound susceptible to Friedel-Crafts reaction in the presence of a catalytic amount of a solid super acid resin catalyst to produce an aryl-substituted higher saturated fatty acid compound as the reaction product.

2. The method of claim 1 which further comprises the step of separating the reaction product from the catalyst.

3. The method of claim 2 wherein the yield of aryl-substituted fatty compound is at least about 80%.

4. The method of claim 3 wherein the catalyst is a perfluorocarbon resin with perfluoro side chain containing sulfonic acid groups.

5. The method of claim 4 wherein from about 0.5 parts by weight to about 5 parts by weight of the catalyst is present per 100 parts by weight of the reactants.

6. A method of preparing an aryl-substituted saturated higher fatty acid comprising bringing into reactive contact oleic acid, linoleic acid and an aromatic compound susceptible to Friedel-Crafts alkylation reaction in the presence of a catalytic amount of a solid perfluorinated resin with perfluoro side chains containing sulfonic acid groups to produce an aryl-substituted saturated higher fatty acid as the reaction product.

7. The method of claim 6 which further comprises the step of separating the reaction product from the catalyst.

8. The method of claim 7 wherein from about 0.5 parts by weight to about 5 parts by weight of the catalyst is present per 100 parts by weight of the reactants.

9. The method of claim 8 wherein the yield of the aryl-substituted compound is at least 80%.

10. The method of claim 7 wherein oleic acid and toluene are the reactants.

11. The method of claim 7 wherein oleic acid and phenol are the reactants.

* * * * *